United States Patent
Jeannin

[11] Patent Number: 6,083,519
[45] Date of Patent: Jul. 4, 2000

[54] N-PHENYLPYRAZOLE-BASED ANTI-FLEA AND ANTI-TICK COLLAR FOR CATS AND DOGS

[75] Inventor: Philippe Jeannin, Tournefeuille, France

[73] Assignee: Merial, Lyon, France

[21] Appl. No.: 09/174,598

[22] Filed: Oct. 19, 1998

Related U.S. Application Data

[60] Division of application No. 08/863,182, May 27, 1997, Pat. No. 5,885,607, which is a continuation-in-part of application No. 08/692,430, Aug. 5, 1996, abandoned.

[30] Foreign Application Priority Data

Mar. 29, 1996 [FR] France ................................. 96 04206
Mar. 26, 1997 [FR] France ................................. 97 03707

[51] Int. Cl.$^7$ .................................................. A01N 25/34
[52] U.S. Cl. ........................ 424/411; 424/405; 424/409; 514/372
[58] Field of Search ................... 424/403–406, 424/409, 411; 514/372

[56] References Cited

U.S. PATENT DOCUMENTS 5,232,940  8/1993  Hatton et al. ............................ 514/407
5,567,429  10/1996  Penbo ...................................... 424/405

FOREIGN PATENT DOCUMENTS 0295117  of 0000  European Pat. Off. .

OTHER PUBLICATIONS

Postal et al. Abstract Veterinary Dermatology vol. 6, 3 pp. 153–158, 1995.
Atwell Abstract Australian Veterinary Practicner vol. 26, 3 pp. 155, 1996.
Geenzhi Abstract Professional Veterinaria 190 1 supplement pp. 19–22, 1995.

*Primary Examiner*—Neil S. Levy
*Attorney, Agent, or Firm*—Frommer Lawrence & Haug LLP; William S. Frommer; Thomas J. Kowalski

[57] ABSTRACT

Collar or other external device for a pet, in particular a cat or dog, made of a matrix in which is incorporated from 0.1 to 40% by weight, preferably from 1 to 15% by weight, relative to the collar, of a substance which is active against ectoparasites such as fleas and ticks, this active substance being formed of at least one compound corresponding to formula (I) below:

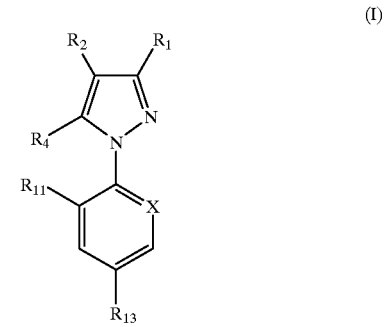

this collar or other external device being designed to ensure more than 6 months of efficacy against fleas and more than 3 months of efficacy against ticks, the efficacy being maintained for several weeks even if the collar or other external device is taken off or lost or if there is a variation in the release of the compound.

13 Claims, No Drawings

N-PHENYLPYRAZOLE-BASED ANTI-FLEA AND ANTI-TICK COLLAR FOR CATS AND DOGS

This is a divisional of application Ser. No. 08/863,182 filed May 27, 1997 now U.S. Pat. No. 5,885,607 which is a continuation-in-part of Ser. No. 08/692,430 filed Aug. 5, 1996 now abandoned.

The present invention relates to an external antiparasitic device, in particular a collar, for pets, in particular cats and dogs, this collar being active against the ectoparasites of these animals, in particular fleas and ticks.

The invention also relates to the use of active compounds for the manufacture of such collars or external devices, as well as to a treatment process relating thereto.

The invention is directed mainly towards fleas of the genus Ctenocephalides, in particular *C. felis* and *C. canis*, and ticks, in particular of the genus Rhipicephalus, especially *sanguineus*, as well as harvest ticks (*Trombicula automnalis*), which are acarids that mainly attack hunting dogs.

Collars intended to eliminate common ectoparasites from cats and dogs have been produced for a long time. These collars consist of a matrix, usually a plastic matrix, which incorporates between 5 and 40% active substance and is capable of releasing it over time. These collars thus theoretically have the aim of ensuring long-lasting protection.

However, despite the activity claims, out in the field the collars do not have the efficacy required to ensure the actual elimination of these parasites. The cause of this may be the low activity of the active substance included in the matrix. Another cause may be the accelerated degradation of these active substances under the effect of climatic factors, such as light, heat and rain. Lastly, control of the release of the active substance from the matrix is largely overevaluated. Release generally proves to be difficult and variable, and may depend greatly on the.manufacturing conditions, which may vary from one batch to another, and on the conditions of use, in particular climatic variations and especially humidity and temperature, etc. In addition, only a relatively small amount of the active substance incorporated is actually released and it proves difficult to be able to control and optimize its release.

Another drawback of the collars encountered in practice arises from the mode of use of this device which may, obviously, be taken off, worn irregularly, or even be pulled off when the animal moves about, for example in undergrowth; the problem is particularly critical for hunting dogs whose collars are removed before a hunting outing even though they will be confronted with a flea- and tick-ridden environment.

Patent applications WO-A-87/03781 and EP-A-0,295,117 have proposed insecticides of the N-phenyl-pyrazole class.

These substances are described as being active against a very large number of parasites encountered in various fields, namely agriculture, public health and human and veterinary medicine. In the latter field, these substances may act in particular against the fleas and ticks of pets, such as cats and dogs. These substances may be applied in various ways, namely via the oral, parenteral, percutaneous or topical route. The latter type of administration itself covers many possibilities, namely sprays, powders, baths, showers, jets, greases, shampoos, creams, waxes, preparations of skin solution type (pour-on) and external devices such as earrings and collars to provide local or systemic treatment. EP-A-0,295,117 and EP-A-0,500,209 propose a slow release composition which may be in the form of a collar or earrings for controlling harmful insects. Such a formulation may comprise from 0.5 to 25% active material, from 75 to 99.5% polyvinyl chloride and a catalytic amount of a plasticizer, dioctyl phthalate.

French patent application FR-A-2,713,889 describes a pesticide composition containing an insect growth regulator and an N-aryldiazole derivative chosen from the derivatives 4-(2-bromo-1,1,2,2-tetrafluoro-ethyl)-1-(3-chloro-5-trifluoromethylpyridine-2-yl)-2-methylimidazole, 5-amino-3-cyano-1-(2,6-dichloro-4-trifluoromethylphenyl)-4-trifluoromethylsulphinylpyrazole and 5-amino-3-cyano-1-(2,6-dichloro-4-trifluoromethylphenyl)-4-trifluoromethylthiopyrazole. As in the prior documents discussed above, the compositions are directed towards a large number of insects in different fields, and various types of formulations. Dog fleas and cat fleas are targeted. Among the formulations proposed, this document mentions resinous preparations which may be made into pesticide collars for animals.

However, none of these documents describes the use of pesticidal collars comprising a compound of the N-phenylpyrazole family to control fleas and ticks on pets such as cats and dogs, which make it possible to ensure a high level of efficacy for a long period against these parasites.

As for the pesticidal compounds of the prior art, a specialist might have expected to encounter conventional problems of release from the collars and thus problems of activity.

After all, French patent application FR-A-2,713,889 proposes, does it not, the combination of such compounds with an insect growth regulator?

The publications C. Genchi et al., Professione Veterinaria No. 1, supplement 1995, pages 19 to 22, J. M. Postal, Professione Veterinaria No. 1, supplement 1995, pages 17 and 18 and A. Searle et al., Australian Veterinary Practitioner, volume 25, No. 3, 1995, pages 157 and 158 propose instead to effectively control fleas and ticks using a sprayable solution (spray) containing this type of active compound.

The Applicant has now found, surprisingly, that despite the fact that these N-phenylpyrazoles encounter the same difficulties of release as the products of the prior art, it is however possible to obtain collars which are entirely effective for the elimination of cat and dog ectoparasites over a very long period, for example from 6 to 18 months, and that, in addition, the efficacy persists long after the collar is taken off, namely over a period which may be equal to or exceed 2 months, such that it is then possible to obtain a collar which is entirely effective irrespective of the conditions of use. On account of the fact that the protection persists after the collar is taken off, it may be understood that irregular or voluntary use or that resulting from loss of the collar does not jeopardize the protection from which the animal should benefit.

In addition, the Applicant has observed that this long-lasting efficacy was obtained with concentrations of active substance in the matrix forming the collar which were much smaller than those of the standard products. It was also observed that this efficacy was obtained within a very short time of the collars being put on, in particular an efficacy of greater than 95% in 24 h against fleas and greater than 90% in 48 h against ticks.

It was observed, very surprisingly, that the compounds according to the invention, which are very lipophilic and of high vapour pressure (low volatility), had a very high affinity for the sebum which usually covers the animal's coat (skin and hair), such that, when released, this compound is taken up by the sebum, after which a translocation phenomenon occurs ensuring distribution of active substance over the animal's entire body. In addition, and this is a noteworthy point, these active substances become concentrated in the sebaceous glands which become a reservoir for them, ensuring very long-lasting efficacy and making it possible to compensate for the absence of the collar, by releasing the active substance by passive diffusion.

By virtue of this phenomenon, the variations in release of the active substance by the collar on account of, for example, a variation in climatic conditions, are compensated for by the possibilities of release by the sebaceous glands.

It was also observed that after a bath, which could possibly lead to the removal of the sebum distributed over the animal's body, the animal very rapidly became reprotected, in the presence or absence of the collar, owing to the fact that secretion of new sebum is accompanied by a release, by the sebaceous glands, of the active substance that they contain.

The subject of the present invention is thus a collar or other external device for a pet, in particular a cat or dog, made of a matrix in which is incorporated from 0.1 to 40% by weight, relative to the collar, of a substance which is active against ectoparasites such as fleas and ticks (anti-flea and anti-tick collar or other external device), this active substance being formed of at least one compound corresponding to formula (I) below:

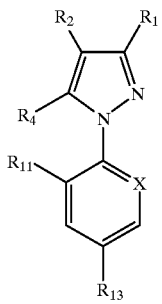

(I)

in which:
$R_1$ is CN or methyl or a halogen atom;
$R_2$ is $S(O)_n R_3$ or 4,5-dicyanoimidazol-2-yl or haloalkyl;
$R_3$ is alkyl or haloalkyl;
$R_4$ represents a hydrogen or halogen atom; or a radical $NR_5R_6$, $S(O)_m R_7$, $C(O)R_7$, $C(O)O$—$R_7$, alkyl, haloalkyl or $OR_8$, or a radical —N=$C(R_9)(R_{10})$;
$R_5$ and $R_6$ independently represent a hydrogen atom or an alkyl, haloalkyl, C(O)alkyl, alkoxycarbonyl or $S(O)_r CF_3$ radical; or $R_5$ and $R_6$ may together form a divalent alkylene radical which may be interrupted by one or two divalent hetero atoms, such as oxygen or sulphur;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups such as OH, —O-alkyl, —S-alkyl, cyano or alkyl;
$R_{11}$ and $R_{12}$ represent, independently of each other, a hydrogen or halogen atom, or optionally CN or $NO_2$;
$R_{13}$ represents a halogen atom or a haloalkyl, haloalkoxy, $S(O)_q CF_3$ or $SF_5$ group;

m, n, q and r represent, independently of each other, an integer equal to 0, 1 or 2;
X represents a trivalent nitrogen atom or a radical C—$R_{12}$, the other three valency positions of the carbon atom forming part of the aromatic ring;
with the proviso that when $R_1$ is methyl, either $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is =C—Cl;

this collar or other external device being designed to ensure at least more than 6 months of efficacy against fleas and at least more than 3 months of efficacy against ticks, the efficacy preferably being maintained for several weeks even if the collar or other external device is taken off or lost or if there is a variation in the rate of release of the compound (I) by the matrix.

Preferably, in formula (I),
$R_1$ is CN or methyl;
$R_2$ is $S(O)_n R_3$;
$R_3$ is alkyl or haloalkyl;
$R_4$ represents a hydrogen or halogen atom; or a radical $NR_5R_6$, $S(O)_m R_7$, $C(O)R_7$, alkyl, haloalkyl or $OR_8$ or a radical —N=$C(R_9)(R_{10})$;
$R_5$ and $R_6$ independently represent a hydrogen atom or an alkyl, haloalkyl, C(O)alkyl or $S(O)_r CF_3$ radical; or $R_5$ and $R_6$ may together form a divalent alkylene radical which may be interrupted by one or two divalent hetero atoms, such as oxygen or sulfur;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups such as OH, —O-alkyl, —S-alkyl, cyano or alkyl;
$R_{11}$ and $R_{12}$ represent, independently of each other, a hydrogen or halogen atom;
$R_{13}$ represents a halogen atom or a haloalkyl, haloalkoxy, $S(O)_q CF_3$ or $SF_5$ group;
m, n, q and r represent, independently of each other, an integer equal to 0, 1 or 2;
X represents a trivalent nitrogen atom or a radical C—$R_{12}$, the other three valency positions of the carbon atom forming part of the aromatic ring;
with the proviso that when $R_1$ is methyl, then $R_3$ is haloalkyl, $R_4$ is $NH_2$, $R_{11}$ is Cl, $R_{13}$ is $CF_3$ and X is N.

Compounds of formula (I) in which $R_1$ is CN will be selected most particularly. The compounds in which $R_2$ is $S(O)_n R_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. Compounds in which $R_{11}$ is a halogen atom and those in which $R_{13}$ is haloalkyl, preferably $CF_3$, are also preferred. In the context of the present invention, compounds combining two or more of these characteristics will advantageously be selected.

A preferred class of compounds of formula (I) consists of compounds such that $R_1$ is CN, $R_3$ is haloalkyl, preferably $CF_3$, or ethyl, $R_4$ is $NH_2$, $R_{11}$ and $R_{12}$ are, independently of each other, a halogen atom, and/or $R_{13}$ is haloalkyl.

In the present invention, the alkyl radicals may contain generally from 1 to 6 carbon atoms. The cycle formed by the divalent alkylene radical representing $R_5$ and $R_6$, as well as with the nitrogen atom to which $R_5$ and $R_6$ are linked may be generally a cycle of 5, 6 or 7 links.

A compound of formula (I) which is most particularly preferred in the invention is 1-[2,6-Cl$_2$4-CF$_3$phenyl]3-CN 4-[SO—CF$_3$]5-NH$_2$pyrazole,
which is referred to hereinbelow as compound A.

Mention may also be made of the two compounds which differ from the above A by the following characteristics:
1- n=0, R$_3$=CF$_3$
2- n=1, R$_3$=ethyl.

Compounds of formula (I) may be prepared according to one or other of the processes described in patent applications WO-A-87/3781, 93/6089, 94/21606 or European patent application EP-A-0,295,117, or any other process falling within the competence of a specialist skilled in the art of chemical synthesis. For the chemical preparation of the products of the invention, a person skilled in the art is considered as having at his disposal, inter alia, all of the contents of "Chemical Abstracts" and the documents which are cited therein.

However, low concentrations, of from 1 to 15% by weight and more particularly, especially for compound A, of from 1.25 to 10%, are preferred.

Under optimum conditions, compound (I) and especially compound A is present in the collar in a proportion of from 2 to 6% by weight, more particularly from 2.5 to 5% by weight.

It would obviously be possible to add to compound A any other insecticide which might be considered useful.

These insecticides may be present in the same matrix as the compound according to the invention. A composite collar made of at least two parts, each including a different active substance, may also be used.

Within the scope of the invention, matrices usually used to make collars may be used. Preferred examples which may be mentioned are matrices based on PVC (polyvinyl chloride), as described in U.S. Pat. Nos. 3,318,769, 3,852,416 and 4,150,109 and 5,437,869, and other vinyl polymers.

The plasticizers may be chosen in particular from adipates, phthalates, phosphates and citrates.

One or more plasticizers will preferably be added to the PVC, these plasticizers being chosen in particular from the following compounds:

diethyl phthalate
dioctyl sebacate
dioctyl adipate
diisodecyl phthalate
acetyl tributyl citrate
diethyl hexyl phthalate
di-n-butyl phthalate
benzyl butyl phthalate
acetyl tributyl citrate
tricresyl phosphate
2-ethylhexyl diphenyl phosphate.

Even more preferably, a PVC matrix will be used in the presence of a primary remanent plasticizer and a secondary plasticizer, in particular according to EP-A-0,539,295 and EP-A-0,537,998.

Among the secondary plasticizers, mention may be made of the following products:

acetyl triethyl citrate
triethyl citrate
triacetin
diethylene glycol monoethyl ether
triphenyl phosphate.

A common stabilizer may also be added thereto.

For the purposes of the present invention, the term external device should be understood to refer to any device which can be attached externally to the animal in order to provide the same function as a collar.

By varying the concentration and/or composition of the matrix, collars or other external devices according to the invention, which ensure effective and long-lasting protection against fleas, may be made. Collars or other external devices may be made with an efficacy of greater than 6 months, in particular of greater than or equal to 12 or 18 months, even when the collar or external device is taken off for a relatively prolonged period. When the collar or device is taken off, the duration of effective protection may range from 2 to 3 months.

By varying the concentration and/or composition of the matrix, it is possible to.make collars or other external devices according to the invention which ensure effective and long-lasting protection against ticks. Collars or external devices may be made with an efficacy of greater than 3 months, in particular of greater than or equal to 12 or 15 months, even when the collar or external device is taken off for a relatively prolonged period. When the collar or external device is taken off, the duration of effective protection may range from 1 to 2 months.

It is noteworthy that this very long-lasting and total efficacy is obtained by the compound according to the invention alone, without addition of another insecticide.

The subject of the present invention is also a method for eliminating ectoparasites, in particular fleas and ticks, from pets such as cats and dogs, in which method at least one collar or other external device in accordance with the invention is attached to the animal and the animal is afforded long-lasting, effective protection against these parasites, even when the collar or other external device is taken off. The method is capable of ensuring prevention and treating fleas and ticks to a high degree of efficacy and over a period exceeding 6 months against fleas and 3 months against ticks, the efficacy preferably being maintained over several weeks even if the collar or external device is taken off or if there is a variation in the release of the compound (I) by the collar or external device. The indications of duration have been given above. Preferably, it is recommended that, in accordance with the method according to the invention, after it has been put on for the first time, the collar or external device should remain on the animal for at least 24 hours in order for sufficient active substance to pass to the animal and for the sebaceous glands to have been able to store this active substance.

The object of this method is non-therapeutic and in particular relates to the cleaning of animal hairs and skin by elimination of the parasites which are present, as well as their residues and dejections. The treated animals thus have hair which is more pleasant to look at and to feel.

The invention also relates to such a method for therapeutic purposes, intended to treat and prevent parasitoses having pathogenic consequences.

The subject of the present invention is also the use of a compound corresponding to formula I for the production of a collar or other external device intended to be attached to a pet, in particular cats and dogs, this compound being capable of ensuring prevention and treating fleas and ticks to a high degree of efficacy and over a period exceeding 6 months against fleas and 3 months against ticks, the efficacy preferably being maintained for several weeks if the collar or the external device is taken off or lost or if there is a variation in the release of the compound (I) by the collar or the external device. The devices as above are concerned.

In particular, the method and device according to the invention are designed to provide for an efficacy of greater than 95%, or even greater than 98 or 99% against fleas.

For ticks, the desired efficacy exceeds 80% or 90%.

Similarly, the invention, against fleas, is directed towards the production of a long-lasting efficacy, cacy, longer than or equal to 12 months and even to 18 months.

For ticks, this duration is longer than 12 months, or even longer than 15 months.

Also preferably, the invention is directed towards the production of collars or other external devices which make it possible to obtain an efficacy maintained in the absence of the collar or external device over a period ranging from 2 to 3 months, or more, against fleas and from 1 to 2 months, or more, against ticks.

The present invention will now be described in greater detail with the aid of non-limiting examples from which other particular features and advantages of the invention will emerge.

EXAMPLE 1

| Collar containing 10% compound A |  |  |
| --- | --- | --- |
| The following two types of collar were prepared (mixing and then extrusion) | | |
| Formulation 1: | PVC | 50.0% |
|  | Stabilizer | 0.5% |
|  | Epoxidized soybean oil | 5.0% |
|  | Diisooctyl adipate | 34.5% |
|  | Compound A | 10.0% |
| Formulation 2: | PVC | 50.0% |
|  | Stabilizer | 0.5% |
|  | Epoxidized soybean oil | 5.0% |
|  | 2-Ethylhexyl diphenyl phosphate | 34.5% |
|  | Compound A | 10.0% |

(% by weight).

For the tests, 9 adult dogs which had not received any insecticide or acaricide for at least 40 days were chosen. The dogs were washed with an insecticide-free shampoo and combed in order to remove any existing parasites.

The dogs were divided into groups of three.
Group A
Untreated controls
Group B
Collar containing 10% compound A—formulation 1.
Group C
Collar containing 10% compound A—formulation 2.

The dogs are infested with about 100±10 *Ctenocephalides felis* cat fleas (Unfed cat fleas) and 50±2 *Rhipicephalus sanguineus* ticks (Brown dog tick).

The treatment follows the following general schema:
DAY
−2 Infestation with the fleas and ticks.
0 Collars are put on.
2 Fleas and ticks are counted with a comb.
7 Infestation with ticks.
8 Infestation with fleas.
9 Counting with a comb
35 Infestation with ticks.
36 Infestation with fleas.
37 Counting with a comb.
63 Infestation with ticks.
64 Infestation with fleas.
65 Counting with a comb.

The same process is continued with infestation with fleas and ticks every month for as long as a satisfactory efficacy is observed.

Hair samples were taken on

D 205 and D 261 for all the dogs.

The collars were taken off on D 149 on dogs 363 and 289, on D 177 for dogs 87 and 300 and on D 205 for dogs 256 and 335.

The concentrations of active substance according to the invention on the hairs which were obtained at D 205 and D 261 are presented in Tables 1 and 2 respectively, in µg/g of hair.

TABLE 1

Concentration of active substance accoraing to the invention on D 205.

| | CONCENTRATION ($\mu g \cdot g^{-1}$) | | | | |
| --- | --- | --- | --- | --- | --- |
| DOG No. | UNDER THE COLLAR | RIGHT FLANK | LEFT FLANK | MIDDLE OF BACK | LUMBAR REGION |
| GROUP B | | | | | |
| 363 | 18.63 | 3.11 | 2.33 | 1.73 | 6.99 |
| 87 | 19.03 | 2.28 | 3.08 | 5.81 | 4.54 |
| 256 | 14.66 | 3.04 | 3.01 | 2.48 | 10.99 |
| GROUP C | | | | | |
| 289 | 27.47 | 11.75 | 15.19 | 8.99 | 30.9 |
| 300 | 482.4 | 34.6 | 15.69 | 17.97 | 36.7 |
| 335 | 257.4 | 23.86 | 28.86 | 22.8 | 41.2 |

TABLE 2

Concentration of active substance accoraing to the invention, on hairs on D 261.

| | CONCENTRATION ($\mu g \cdot g^{-1}$) | | | | |
| --- | --- | --- | --- | --- | --- |
| DOG No. | UNDER THE COLLAR | RIGHT FLANK | LEFT FLANK | MIDDLE OF BACK | LUMBAR REGION |
| GROUP B | | | | | |
| 363 | 0.94 | 0.65 | >0.29 | >0.39 | 1.47 |
| 87 | 0.64 | 0.94 | >0.32 | >0.40 | ND |
| 256 | >0.97 | ND | 0.81 | 0.78 | 0.69 |
| GROUP C | | | | | |
| 289 | 3.16 | >0.75 | >0.59 | >0.60 | 2.03 |
| 300 | 3.79 | >0.70 | 2.04 | 1.35 | 5.52 |
| 335 | 1.84 | 1.67 | 2.99 | 4.61 | 4.19 |

ND = Not determined.

A distribution of active substance over the hair is observed: the concentrations on the different areas are higher with the formulation of Group C and are relatively homogeneous from one area to another.

The concentrations of active substance are still detectable 16 weeks after the collar has been taken off and are still effective at that stage.

Tables 3, 4 and 5 make it possible to carry out a concentration/activity correlation.

TABLE 3

Concentration/activity relationship on D 149.

| DOG No. | CONCENTRATION ($\mu g \cdot g^{-1}$) UNDER THE COLLAR | BACK AND FLANKS AV. | BACK AND FLANKS MIN | BACK AND FLANKS MAX | ACTIVITY[1] FLEAS | ACTIVITY[1] TICKS |
|---|---|---|---|---|---|---|
| GROUP B | | | | | | |
| 363 | 559.5 | 15.6 | 10.7 | 24.8 | 0 | 1 |
| GROUP C | | | | | | |
| 289 | 871.3 | 48.9 | 30.8 | 94.4 | 0 | 0 |

[1]Number of fleas and ticks present on the dog

TABLE 4

Concentration/activity relationship on D 205.

| DOG No. | CONCENTRATION ($\mu g \cdot g^{-1}$) UNDER THE COLLAR | BACK AND FLANKS AV. | BACK AND FLANKS MIN | BACK AND FLANKS MAX | ACTIVITY[1] FLEAS | ACTIVITY[1] TICKS |
|---|---|---|---|---|---|---|
| GROUP B | | | | | | |
| 363 | 18.6 | 3.54 | 1.73 | 6.99 | 0 | 12 |
| 87 | 19.0 | 3.93 | 2.28 | 5.81 | 0 | 22 |
| 256 | 15.0 | 4.88 | 2.48 | 11.0 | 0 | 15 |
| GROUP C | | | | | | |
| 289 | 27.5 | 16.7 | 8.99 | 30.9 | 0 | 12 |
| 300 | 482.4 | 26.3 | 15.7 | 36.7 | 0 | 0 |
| 335 | 257.4 | 29.2 | 22.8 | 41.2 | 0 | 0 |

[1]Number of fleas and ticks present on the dog

TABLE 4

Concentration/activity relationship on D 261.

| DOG No. | CONCENTRATION ($\mu g \cdot g^{-1}$) UNDER THE COLLAR | BACK AND FLANKS AV. | BACK AND FLANKS MIN | BACK AND FLANKS MAX | ACTIVITY[1] FLEAS | ACTIVITY[1] TICKS |
|---|---|---|---|---|---|---|
| GROUP B | | | | | | |
| 363 | 0.94 | >0.70 | >0.29 | 1.47 | 0 | 21 |
| 87 | 0.64 | <0.55 | <LOQ | 0.94 | 0 | 12 |
| 256 | >0.97 | <0.76 | <LOQ | 0.81 | 1 | 24 |
| GROUP C | | | | | | |
| 289 | 3.16 | >0.99 | >0.59 | 2.03 | 0 | 28 |
| 300 | 3.79 | >2.40 | >0.70 | 5.52 | 0 | 19 |
| 335 | 1.84 | 3.37 | 1.67 | 4.61 | 0 | 3 |

[1]Number of fleas and ticks present on the dog
AV. = average
MIN = minimum
MAX = maximum
LOQ = limit of quantification = 0.25 $\mu g/g$ On D 261, the activity towards fleas is 100% on all the dogs, except for one dog (presence of a flea).

The minimum concentrations (on the hair) which are effective towards fleas and ticks are determined to be about:

20 micrograms per gram of hair for ticks 1 microgram per gram of hair for fleas.

An activity of at least 5 months for ticks and of at least 9 months for fleas is observed with these formulations.

EXAMPLE 2

Dogs were divided up into 6 groups of 8 dogs

A: Control group: collar containing no active substance.

B: Reference product: commercial collar against fleas and ticks, containing 8% Chlorpyrifos (O,O-diethyl-O-(3,5,6-trichloro-2-pyridyl)phosphorothioate), referred to as ref. in the tables.

C: Collar containing 2.5% compound A.

D: Collar containing 5% compound A.

E: Collar containing 10% compound A

The collars were made with the same ingredients as in formulation 2 of Example 1, with, in addition, a pigment (titanium dioxide).

The tests follow the following schedule:

−2 Infestation with fleas and ticks

0 Collars are put on

2 Counting with a comb

7 Reinfestation with ticks

8 Reinfestation with fleas

9 Counting with a comb

35 Reinfestation with ticks

36 Reinfestation with fleas

37 Counting with a comb

The process is continued along these lines from month to month.

Infestations and reinfestations are carried out at a rate of:

100±10 fleas

50±3 ticks

Tables 6 and 7 give the average effectiveness results.

TABLE 6

Percentage effectiveness on fleas, calculated as a geometric mean

| | GROUPS TREATED | | | |
|---|---|---|---|---|
| DAY | Ref. 8% | 2.5% | 5% | 10% |
| −5 | 0.0% | 9.3% | 0.0% | 0.0% |
| 2 | 63.9% | 98.7% | 100.0% | 100.0% |
| 9 | 96.3% | 100.0% | 100.0% | 100.0% |
| 37 | 96.1% | 99.9% | 100.0% | 100.0% |
| 65 | 99.1% | 100.0% | 100.0% | 100.0% |
| 93 | 99.6% | 100.0% | 100.0% | 100.0% |
| 121 | 99.4% | 100.0% | 100.0% | 100.0% |
| 149 | 98.3% | 100.0% | 100.0% | 100.0% |
| 177 | 97.9% | 100.0% | 100.0% | 100.0% |
| 205 | 98.5% | 100.0% | 100.0% | 100.0% |
| 233 | 96.6% | 100.0% | 100.0% | 100.0% |
| 268 | 89.6% | 100.0% | 100.0% | 100.0% |
| 289 | 68.4% | 100.0% | 100.0% | 100.0% |
| 317 | 76.0% | 100.0% | 100.0% | 100.0% |
| 345 | 79.5% | 100.0% | 100.0% | 100.0% |
| 373 | — | 100.0% | 100.0% | 100.0% |
| 401 | — | 99.4% | 100.0% | 99.8% |
| 429 | — | 99.2% | 99.8% | 99.3% |
| 457 | — | 96.9% | 98.8% | 99.2% |
| 485 | — | 96.7% | 98.2% | 98.7% |
| 513 | — | 90.3% | 99.0% | 99.3% |
| 541 | — | — | 98.8% | 100.0% |

TABLE 7

Percentage effectiveness on ticks, calculated as a geometric mean

| | | GROUPS TREATED | | |
|---|---|---|---|---|
| DAY | Ref. 8% | 2.5% | 5% | 10% |
| −5 | 4.7% | 19.1% | 19.1% | 32.0% |
| 2 | 34.5% | 67.0% | 100.0% | 98.5% |
| 9 | 86.9% | 96.2% | 100.0% | 100.0% |
| 37 | 0.0% | 27.2% | 95.4% | 95.4% |
| 65 | 31.7% | 85.0% | 100.0% | 95.8% |
| 93 | 31.8% | 86.7% | 100.0% | 95.7% |
| 121 | 65.2% | 91.3% | 88.8% | 92.1% |
| 149 | 59.0% | 93.4% | 92.0% | 94.5% |
| 177 | 67.2% | 84.9% | 95.3% | 95.2% |
| 205 | 62.0% | 86.2% | 100.0% | 98.4% |
| 233 | 62.6% | 89.8% | 98.3% | 97.9% |
| 268 | 57.5% | 77.4% | 98.2% | 99.5% |
| 289 | 44.6% | 92.4% | 97.2% | 95.1% |
| 317 | — | 74.5% | 85.6% | 92.4% |
| 345 | — | 88.1% | 98.8% | 98.0% |
| 373 | — | 72.4% | 93.9% | 95.7% |
| 401 | — | 63.4% | 98.5% | 93.6% |
| 429 | — | 75.3% | 83.2% | 93.3% |
| 457 | — | 62.4% | 84.1% | 86.7% |
| 485 | — | — | — | — |
| 513 | — | — | — | — |
| 541 | — | — | — | — |

I claim:

1. A method for distributing an active agent over a pet's body and/or in sebaceous glands of the pet and thereby control fleas and ticks on or eliminate fleas and ticks from the pet to ensure more than six months of efficacy of greater than 95% against fleas, as determined in a test providing the reinfestation of the pet with 100±10 fleas, and more than three months of efficacy of greater than 90% against ticks, as determined in a test providing the reinfestation of the pet with 50±3 ticks, comprising attaching to the pet a collar having a matrix into which is incorporated from 0.1 to 40% by weight, relative to the collar, of the active agent against fleas and ticks, wherein this active agent comprises at least one compound corresponding to formula (I) below in which $R_1$ is CN, $R_2$ is $S(O)_nR_3$, $R_3$ is haloalkyl, $R_4$ is $NH_2$, X is C-R$_{12}$, $R_{12}$ is a halogen atom, $R_{11}$, is a halogen atom, $R_{13}$ is haloalkyl, and n is an integer equal to 0, 1 or 2

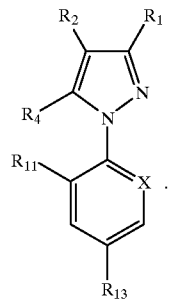

2. A method for distributing an active agent over a pet's body and/or in sebaceous glands of the pet and thereby control fleas and ticks on or eliminate fleas and ticks from the pet to ensure more than six months of efficacy of greater than 95% against fleas, as determined in a test providing the reinfestation of the pet with 100±10 fleas, and more than three months of efficacy of greater than 90% against ticks, as determined in a test providing the reinfestation of the pet with 50±3 ticks, comprising attaching to the pet a collar having a matrix into which is incorporated from 0.1 to 40% by weight, relative to the collar, of the active agent against fleas and ticks, wherein this active agent comprises 1-[2,6-$Cl_2$4-$CF_3$phenyl]3-CN4-[SO—$CF_3$]5-$NH_2$ pyrazole, and whose common name is Fipronil.

3. The method according to claim 1 wherein $R_{13}=CF_3$.

4. The method of claim 1 or 2 wherein the active agent is present in an amount of from 1 to 15% by weight.

5. The method of claim 1 or 2 wherein the active agent is present in an amount of from 1.25 to 10% by weight.

6. The method of claim 1 or 2 wherein the active agent is present in an amount of from 2 to 6% by weight.

7. The method of claim 1 or 2 wherein the active agent is present in an amount of from 2.5 to 5% by weight.

8. The method of claim 1 or 2 wherein the active agent is present in an amount of from 1.25 to 10% by weight.

9. The method of claim 1 or 2 wherein the efficacy is at least 12 months against fleas.

10. The method of claim 1 or 2 wherein the efficacy is at least 18 months against fleas.

11. The method of claim 1 or 2 wherein the efficacy is at least 12 months against ticks.

12. The method of claim 1 or 2 wherein the efficacy is at least 15 months against ticks.

13. The method of claim 1 or 2, wherein the efficacy is maintained over periods of from 2 to 3 months against ticks and from 1 to 2 months against ticks after the collar is removed.

* * * * *

US006083519C1

(12) EX PARTE REEXAMINATION CERTIFICATE (8509th)
United States Patent
Jeannin

(10) Number: US 6,083,519 C1
(45) Certificate Issued: *Sep. 6, 2011

(54) N-PHENYLPYRAZOLE-BASED ANTI-FLEA AND ANTI-TICK COLLAR FOR CATS AND DOGS

(75) Inventor: Philippe Jeannin, Tournefeuille (FR)

(73) Assignee: Merial, Lyons (FR)

Reexamination Request:
No. 90/010,923, Mar. 19, 2010

Reexamination Certificate for:
Patent No.: 6,083,519
Issued: Jul. 4, 2000
Appl. No.: 09/174,598
Filed: Oct. 19, 1998

(*) Notice: This patent is subject to a terminal disclaimer.

Related U.S. Application Data

(60) Division of application No. 08/863,182, filed on May 27, 1997, now Pat. No. 5,885,607, which is a continuation-in-part of application No. 08/692,430, filed on Aug. 5, 1996, now abandoned.

(30) Foreign Application Priority Data

Mar. 29, 1996 (FR) .............................. 96 04206
Mar. 26, 1997 (FR) .............................. 97 03707

(51) Int. Cl.
*A01N 25/34* (2006.01)

(52) U.S. Cl. .................... 424/411; 424/405; 424/409; 514/372

(58) Field of Classification Search .................. None
See application file for complete search history.

(56) References Cited

U.S. PATENT DOCUMENTS

| | | | |
|---|---|---|---|
| 3,852,416 A | 12/1974 | Grubb et al. ................ 424/14 |
| 4,543,247 A | 9/1985 | Von Bittera et al. | |
| 4,774,254 A | 9/1988 | Stetter et al. ............... 514/404 |
| 4,804,675 A | 2/1989 | Jensen-Korte et al. ...... 514/675 |
| 5,104,994 A | 4/1992 | Roberts et al. ............. 548/376 |
| 5,232,940 A | 8/1993 | Hatton et al. | |
| 5,306,694 A | 4/1994 | Phillips et al. ............. 504/253 |
| 5,411,737 A | 5/1995 | Hsu et al. | |
| 5,437,869 A * | 8/1995 | Kelley ........................ 424/406 |

FOREIGN PATENT DOCUMENTS

| | | |
|---|---|---|
| EP | 0500209 A1 | 8/1992 |
| EP | 0537998 A1 | 4/1993 |
| EP | 0639330 A1 | 2/1995 |
| WO | WO 87/03781 A1 | 7/1987 |
| WO | WO 93/60089 A1 | 4/1993 |

OTHER PUBLICATIONS

Genchi et al. Efficacia del fipronil in formulazione spray (Frontline RM) nel trattamento delle infestazioni da pulci e da zecche nel cane, Professione Veterinaria, (1995) No. i, Supplement, pp. 19–22. (English translation).*
Maddison, J.E., et al., (2008) *Small Animal Clinical Pharmacology* (2d ed., Elsevier Limited), p. 223.
Emsworth "Extended Efficacy Spectrum of Azole Pesticides," Research Disclosure, No. 380, Dec. 1, 1995.
Abstract—Postal, J.M., "Efficacia di una Formulazione Spray a Base di Fipronil Allo 0.25% nel Trattamento Delle Infestazione da Pulci e da Zecche Nel Cane," Professione Veterinaria, No. 1, pp. 19–22, (1995).
Searle, A. et al. "Results of Trial of Fipronil as an Adulticide on Ticks (*ixodes holocylclus*) Naturally Attached to Animals in the Brisbane Area," Australian Veterinary Practitioner, 1995, 25(3), 157–158.

* cited by examiner

*Primary Examiner* — Bruce Campell

(57) ABSTRACT

Collar or other external device for a pet, in particular a cat or dog, made of a matrix in which is incorporated from 0.1 to 40% by weight, preferably from 1 to 15% by weight, relative to the collar, of a substance which is active against ectoparasites such as fleas and ticks, this active substance being formed of at least one compound corresponding to formula (I) below:

this collar or other external device being designed to ensure more than 6 months of efficacy against fleas and more than 3 months of efficacy against ticks, the efficacy being maintained for several weeks even if the collar or other external device is taken off or lost or if there is a variation in the release of the compound.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3 are cancelled.

Claims 2 and 4-13 are determined to be patentable as amended.

New claims 14-19 are added and determined to be patentable.

2. A method for distributing an active agent over a pet's body and/or in sebaceous glands of the pet and thereby control fleas and ticks on or eliminate fleas and ticks from the pet to ensure more than six months of efficacy of greater than 95% against fleas, as determined in a test providing the reinfestation of the pet with 100±10 fleas, and more than three months of efficacy of greater than 90% against ticks, as determined in a test providing the reinfestation of the pet with 50±3 ticks, comprising attaching to the pet a collar having a matrix into which is incorporated from 0.1 to 40% by weight, relative to the collar, of the active agent against fleas and ticks, wherein this active agent comprises 1-[2,6-$Cl_2$4-$CF_3$phenyl]3-CN4-[SO-$CF_3$]5-$NH_2$ pyrazole, and whose common name is Fipronil, *wherein said distributing is by translocation*.

4. The method of claim [1 or] 2 wherein the active agent is present in an amount of from 1 to 15% by weight.

5. The method of claim [1 or] 2 wherein the active agent is present in an amount of from 1.25 to 10% by weight.

6. The method of claim [1 or] 2 wherein the active agent is present in an amount of from 2 to 6% by weight.

7. The method of claim [1 or] 2 wherein the active agent is present in an amount of from 2.5 to 5% by weight.

8. The method of claim [1 or] 2 wherein the active agent is present in an amount of from 1.25 to 10% by weight.

9. The method of claim [1 or] 2 wherein the efficacy is at least 12 months against fleas.

10. The method of claim [1 or] 2 wherein the efficacy is at least 18 months against fleas.

11. The method of claim [1 or] 2 wherein the efficacy is at least 12 months against ticks.

12. The method of claim [1 or] 2 wherein the efficacy is at least 15 months against ticks.

13. The method of claim [1 or] 2, wherein the efficacy is maintained over periods of from 2 to 3 months against [ticks] *fleas* and from 1 to 2 months against ticks after the collar is removed.

*14. The method of claim 2, wherein the matrix is based on a vinyl polymer.*

*15. The method of claim 14, wherein the matrix is based on polyvinyl chloride.*

*16. The method of claim 2, wherein the collar comprises one or more plasticizers.*

*17. The method of claim 16, wherein the plasticizer is an adipate, a phthalate, a phosphate or a citrate.*

*18. The method of claim 16, wherein the collar further comprises a secondary plasticizer, and wherein the secondary plasticizer is acetyl triethyl citrate, triethyl citrate, triacetin, diethylene glycol monoethyl ether or triphenyl phosphate.*

*19. The method of claim 17, wherein the collar further comprises epoxidized soybean oil.*

\* \* \* \* \*